United States Patent
Neumann (10) Patent No.: US 6,632,839 B2
(45) Date of Patent: *Oct. 14, 2003

(54) CAPSICUM BASED DISINFECTANT AND STERILIZANT

(76) Inventor: Robert H. Neumann, 1530 Arroyo Ave., San Carlos, CA (US) 94070

( * ) Notice: Subject to any disclaimer, the term of this patent is extended or adjusted under 35 U.S.C. 154(b) by 38 days.

This patent is subject to a terminal disclaimer.

(21) Appl. No.: 09/867,940

(22) Filed: May 30, 2001

(65) Prior Publication Data

US 2001/0034964 A1 Nov. 1, 2001

Related U.S. Application Data

(63) Continuation-in-part of application No. 09/747,225, filed on Dec. 22, 2000, now Pat. No. 6,523,298, which is a continuation-in-part of application No. 09/374,548, filed on Aug. 12, 1999, now abandoned, which is a continuation of application No. 08/871,004, filed on Jun. 6, 1997, now Pat. No. 5,937,572.

(51) Int. Cl.⁷ .............................................. A61K 31/16
(52) U.S. Cl. ........................................................ 514/627
(58) Field of Search ........................................ 514/627

(56) References Cited

U.S. PATENT DOCUMENTS

| 312,270 | A | | 2/1885 | Hoaq |
|---|---|---|---|---|
| 5,027,546 | A | | 7/1991 | Tallon |
| 5,165,199 | A | | 11/1992 | Tallon |
| 5,240,708 | A | | 8/1993 | Plummer et al. |
| 5,466,459 | A | | 11/1995 | Wilson |
| 5,514,779 | A | | 5/1996 | Broekaert et al. |
| 5,525,597 | A | | 6/1996 | Hainrihar et al. |
| 5,542,207 | A | | 8/1996 | Morris, Sr. |
| 5,599,803 | A | | 2/1997 | Hainrihar et al. |
| 5,711,953 | A | | 1/1998 | Bassett |
| 5,937,572 | A | * | 8/1999 | Neumann .................. 43/132.1 |
| 6,523,298 | B2 | * | 2/2003 | Neumann .................. 43/132.1 |

OTHER PUBLICATIONS

Download from Hot Pepper Wax, Inc., HotpepperWax–Products, Jan. 8, 2001,31 pages.
Toxicological Aspects of White Mineral Oils and Petrolatums, Penreco Technical Series, 4 pages.
Download from www.Kalsec.com, Products, Capsicum Oleoresins, Jun. 28, 2000, 6 pages.
Penreco, Drakeol 7 light Mineral Oil NF– Product Specification, 10 pages.
Download from www.hort.purdue.edu.com, Peppers: History and Exploitation of a Serendipitous New Crop Discovery, W. hardy Eshbaugh, May 23,1997,22 pages.
Long–Awaited Nonchemical Alternatives to Drywood Termite Control Study Completed Pest Control Operator of California, Summer 1996, 8 pages.
Helix (TM) Xtra, Syngentra product label for seed treatment, 2 pages.

* cited by examiner

*Primary Examiner*—Kevin E. Weddington
(74) *Attorney, Agent, or Firm*—Ray K. Shahani, Esq.

(57) ABSTRACT

A method and formulation for sterilizing and disinfecting surfaces, and for killing bacteria on contact, the sterilizing and disinfecting formulation containing water and between about 0.0001 percent and about 10.0 percent by weight capsicum, the method and formulation particularly adapted for sterilization and disinfecting food and meat stuffs, and for food and meat processing equipment and facilities.

20 Claims, 2 Drawing Sheets

CAPSICUM BASED DISINFECTANT AND STERILIZANT

RELATED APPLICATIONS

This application is a Continuation-In-Part of U.S. patent application Ser. No. 09/747,225 filed Dec. 22, 2000 now U.S. Pat. No. 6,523,298, which is a Continuation-In-Part of U.S. patent application Ser. No. 09/374,548 filed Aug. 12, 1999 now abandoned, which is a Continuation of U.S. Pat. No. 5,937,572 issued Aug. 17, 1999, based on application Ser. No. 08/871,004 filed Jun. 6, 1997.

FIELD OF THE INVENTION

The present invention relates generally to sterilizing agents and disinfectants, insecticides and pesticides and methods for extermination and control of undesirable living organisms. More particularly, the present invention is a novel compound and method for sterilizing and disinfecting materials, in particular raw cut foods and meats, cutting and processing and handling surfaces and related.

BACKGROUND OF THE INVENTION

Presently, much is known about capsicum. A current internet site located on the world wide web at http://chileheads.netimages.com/provides a great deal of background information. Peppers are members of the genus Capsicum, and the family Solanaceae, which include eggplant and tomatoes. The name Capsicum comes from the Greek kapto, which means "to bite".

It is estimated that there are at least 26 species of peppers categorized at present, most of which are found in the wild. There are five species of domesticated peppers: (1) *annuum*, from "annual; this includes most of the common peppers found in markets including bell peppers, jalapeños and New Mexican; (2) *baccatum*, from "berry-like"; these are the aji peppers found commonly in South America; (3) *chinense*, meaning "from China"; this includes the famous habanero, Scotch Bonnets, etc.; (4) *frutescens*, meaning "brushy" and are the tabasco peppers; and (5) *pubescens*, from "hairy"; these are the South American rocoto peppers. References to *annuum* species often include the pod type. Due to easy inbreeding between *annuum*, *chinense* and *frutescens*, there are hundreds of different varieties found throughout the world. All peppers originated in the New World. The origin seems to be in the area of Bolivia and Paraguay in South America. Wild peppers were spread by birds, who are apparently unaffected by the heat of the fruit.

Many varieties of the Capsicum species are not hot, or pungent. Most paprikas grown in Europe and bell peppers grown in the US have little or no pungency. These varieties are used fresh, or often used to color other foods. The wilder varieties, on the other hand, range from mildly to extremely pungent. This is entirely due to the substance capsaicin, or, actually, a group of similar substances called capsaicinoids. Pure capsaicin, or 8-methyl-n-vanillyl-6-nonenamide, is a whitish powder which is soluble in alcohol but insoluble in cold water, which is why drinking water to help alleviate the burning won't work. The capsaicinoids are unique compared to other "spicy" substances such as mustard oil (zingerone and allyl isothiocyanate), black pepper (piperine) and ginger (gingerol) in that capsaicin causes a long-lasting selective desensitization to the irritant pain by repeated doses of a low concentration or a single high concentration dose.

The use of capsicum in an aqueous solution for exterminating termites is completely unknown.

Numerous other uses for chile peppers have been patented. U.S. Pat. No. 5,217,708 teaches an aerosol lachrymator formulation having all natural pepper extracts as the active ingredients. The lachrymator formulations are useful in self-defense devices. The formulations are non-toxic and have a broader spectrum of activity than man-made lachrymators. These aerosol formulations rely on a carbon dioxide propellant.

Numerous applications of capsicum for medicinal or therapeutic purposes, such as in cough drop formulations, analgesics, thermo slimming cosmetic compositions, ache and pain compounds and arthritis compositions are found in U.S. Pat. Nos. 4,980,169, 4,931,277, 4,702,916, 4,795,638, 4,592,912 and 4,271,154. These applications are unrelated to the present invention.

Numerous applications include the use of capsicum to discourage growth of living organisms. U.S. Pat. No. 5,226,380 teaches a covering material for underwater objects such as boat hulls or water intake pipes. The covering includes a waterproof coating such as adhesive or paint containing capsicum derivatives such as cayenne pepper or oleoresin capsicum, with the coating applied to the outer surface of the object to be protected, to repel marine organisms which might otherwise attach themselves to the object.

U.S. Pat. Nos. 5,599,803 and 5,525,597 teach insecticidal compositions, comprising normally-employed insecticides but comprising also an effective activity-enhancing amount of capsaicin or other capsaicinoid, especially in the form of capsicum, which exhibit synergistic effects against numerous insects, including especially bud worms, boll worms, cabbage loopers, army worms, beet army worms, and beetles, and are especially effective on cotton, soybeans, common garden vegetables, and flowers, when sprayed on the insect or its habitat, especially as an aqueous solution, suspension, or emulsion. Larger crop stands may be effectively treated by aerial spraying from the usual crop-dusting airplane.

U.S. Pat. No. 5,514,779 teaches biocidal proteins capable of isolation from seeds have been characterized. The proteins have an amino acid sequence containing the common cysteine/glycine domain of Chitin-binding Plant Proteins but show substantially better activity against pathogenic fungi, a higher ratio of basic amino acids to acidic amino acids, and/or antifungal activity which results in increased hyphal branching. Antimicrobial proteins isolated from Amaranthus, Capsicum, Briza and related species are provided. The proteins show a wide range of antifungal activity and are active against Gram-positive bacteria. DNA encoding the proteins may be isolated and incorporated into vectors. Plants may be transformed with this DNA. The proteins find agricultural or pharmaceutical application as antifungal or antibacterial agents. Transgenic plants expressing the protein will show increased disease resistance.

U.S. Pat. No. 5,240,708 teaches a composition and method for spraying an area to inhibit web growth and discourage spiders, other insects or the like from returning to the sprayed area. The solution includes liquid soap that is blended with oil of anise and coriander oil. Capsicum is then added and completely blended in the soap mixture. The mixture is blended with an acetic acid solution to form the solution.

U.S. Pat. No. 5,544,304 teaches a composition for repelling birds, the composition having as active ingredients finely divided dried pepper from pungent fruits of plants of the genus Capsicum and finely divided dried garlic and typically being diluted by inert, finely divided mineral material or water for application to the earth surface or to growing plants to repel birds given to eating seeds, plants, vegetables, and fruits.

With regard to the prior art teaching the use of capsicum as an adjunct ingredient to an insecticidal composition, all of these compositions include the use of other, toxic, non-capsicum based chemicals. The use of capsicum therein is as an adjunct, not as a replacement. The use of a solution of capsicum alone in water is neither taught nor suggested in any of the relevant prior art available.

In the generally well known and accepted prior art for extermination of termites and other insect infestations, little is known regarding the availability of safe, efficacious and non-toxic to humans formulations or methods. Methyl bromide is a common chemical which does damage to the ozone layer, is volatile and is very toxic to humans. The gas or liquid is injected directly into soil for extermination of, for example, undesirable crop insects. At present, however, the use of methyl bromide is being discontinued due to changes in the law. However, other chemicals also have similar drawbacks—they are either damaging to the environment or are toxic to humans, or any combination of the two.

One non-chemical approach to termite extermination is taught by U.S. Pat. No. 5,165,199 issued Nov. 24, 1992 to Tallon. This invention concerns a non-toxic method of exterminating dry wood termites, fleas, roaches, ants, weevils and the like by utilizing an inert freezing liquid such as liquid nitrogen as the killing agent. The liquid nitrogen is inserted so as to envelop the colony of objectionable organisms until the environment is reduced to a temperature of at least zero degrees Fahrenheit and maintained at that temperature for between 2 to 5 minutes. Unfortunately, this method requires transportation of heavy, compressed gas-type cylinders for containing the freezing cryogenic liquid. Furthermore, the use of such materials is not only expensive but dangerous, and an accident operating the tanks and transfer equipment can cause significant bodily injury to operators and others.

Thus, while it is known that capsicum and pepper-extract containing formulations exhibit properties which repel animals such as ocean crustaceans, crop and plant insects, birds, etc., there is no reference in the prior art to the use of such formulations for exterminating termites or for clearing existing insect and pest infestations from soil or structures.

One of the drawbacks of using aqueous solutions is that they can create splashes, leaks, vapors, steam if heated, fogs or sprays. Handling such materials can be dangerous, difficult, and may require certain equipment including special containers, special pouring and mixing techniques or equipment, specialized protective clothing, for workers, etc. It would be desirable to provide a liquid insecticidal or pesticidal composition which comprises capsicum as the active killing agent along without the drawbacks described above.

As is well known, the use of toxic chemicals to control insects for agricultural purposes causes damage and pollution of the environment. Certain chemicals have become heavily controlled or banned altogether due to the impact on the environment, due to their impact on infants, children and other humans, etc. Dursban (TM), a common and well-known chemical is currently undergoing legislative review, and its future and further use is questionable. Therefore, it is desirable to develop an alternative to Dursban or other chemicals which have a lasting, negative impact on the environment.

In general, the use of chemicals in food processing plants, slaughterhouses and meat processing plants for disinfecting cut animals, ut meat portions, cutting blades, equipment and handling surfaces, etc., is very important. It is important to use chemicals that sterilize and/or disinfect the vegetables, fruits, other types of foods, meats, the cut sides of animals, the cut meats, the cutting equipment and handling equipment and surfaces. Such products are can be liquids, aerosols, powders, etc., which do not leave any unpleasant or otherwise undesirable residues, which is non-toxic to humans, which does not cause any problems with compatibility with any of the equipment, meats or surfaces.

Contamination of surfaces and equipment in slaughterhouses by *E. coli* is a large concern. Nicking or accidentally scratching or slicing the intestinal tract of an animal being slaughtered my require the facility to discard the entire carcass. Given the risk of contamination of other surfaces, other meat, etc., the risk is too great and therefore, control of *E. coli* bacterial contamination is an on-going challenge.

ADVANTAGES AND SUMMARY OF THE INVENTION

Therefore, it is an advantage and an objective of the present invention to provide a safe and economical method for the disinfecting and sterilizing foods and meats, cutting surfaces, blades, cutting equipment, etc.

It is yet a further advantage and objective of the present invention to provide a formulation and method of disinfecting all types of foods, vegetables, fruits, meats, at all stages of their processing, and of all equipment, surfaces and other handling devices associated therewith.

It is yet a further advantage of the present invention to provide a liquid disinfectant and sterilization solution containing capsicum as the active disinfecting and sterilizing agent, which, optionally, avoids the drawbacks spraying, creating fogs or mists during handling, mixing or manufacturing, etc.

It is yet a further object and advantage of the present invention to provide a safe, environmentally friendly, effective disinfectant and sterilizant for controlling fungus, viruses, microorganisms, insects and other pests associated with slaughterhouses and meat processing facilities.

In summary, the present invention is a safe, environmentally friendly, effective disinfectant and sterilizant and method of use for controlling insects and pests associated with slaughterhouses and meat processing facilities. By contacting cut meats, cutting equipment, surfaces, etc., with an aqueous solution containing any operable sterilizing and disinfecting-effective amount of capsicum, the living organism in contact with the disinfecting and sterilizing solution will be killed and/or rendered inert or inactive. Spraying and injecting the disinfecting and sterilizing solution into foods such as cut meats or animals, cutting surfaces, cutting equipment, refrigerators or freezers, handling equipment including processing surfaces and containers, etc., can be sterilized and/or disinfected conveniently.

Adding an inert carrier oil, such as mineral oil, to the composition will render the aqueous solution slightly more viscous, less prone to splashing or spray, and less prone to fogging or misting. The composition can comprise from between 0.1% to about 100% inert carrier oil. Mineral oil is a very common, non-toxic oil which is readily available. Other environmentally safe and food-grade and non-toxic oils or carrier liquids can be used, including various types of mineral oils, castor oil, etc.

One of the major concerns today for any product is its toxicity. Mineral oils and pharmaceutical grades of petrolatum have a long history of wide use by man and controlled tests on animals which attest to their lack of toxicity. Mineral oil has been taken as an internal lubricant for a great many years and both mineral oils and petrolatums have been used as manor ingredients of cosmetics and ointments for an even longer period of time. Passage of the Food Additives Amendment in 1959 let the FDA to require feeding studies with animals on both mineral oils and petrolatums before they could be permitted to be used as additives in food. In fact, many of the hydrocarbons present in mineral oils and petrolatums are also present in many widely distributed natural products, both plant and animal. In general, however, it is still assumed that little if any mineral oil is absorbed if taken internally or externally, but that some indication is given that metabolism of some of the oil components can and may certainly take place.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Figure 1:
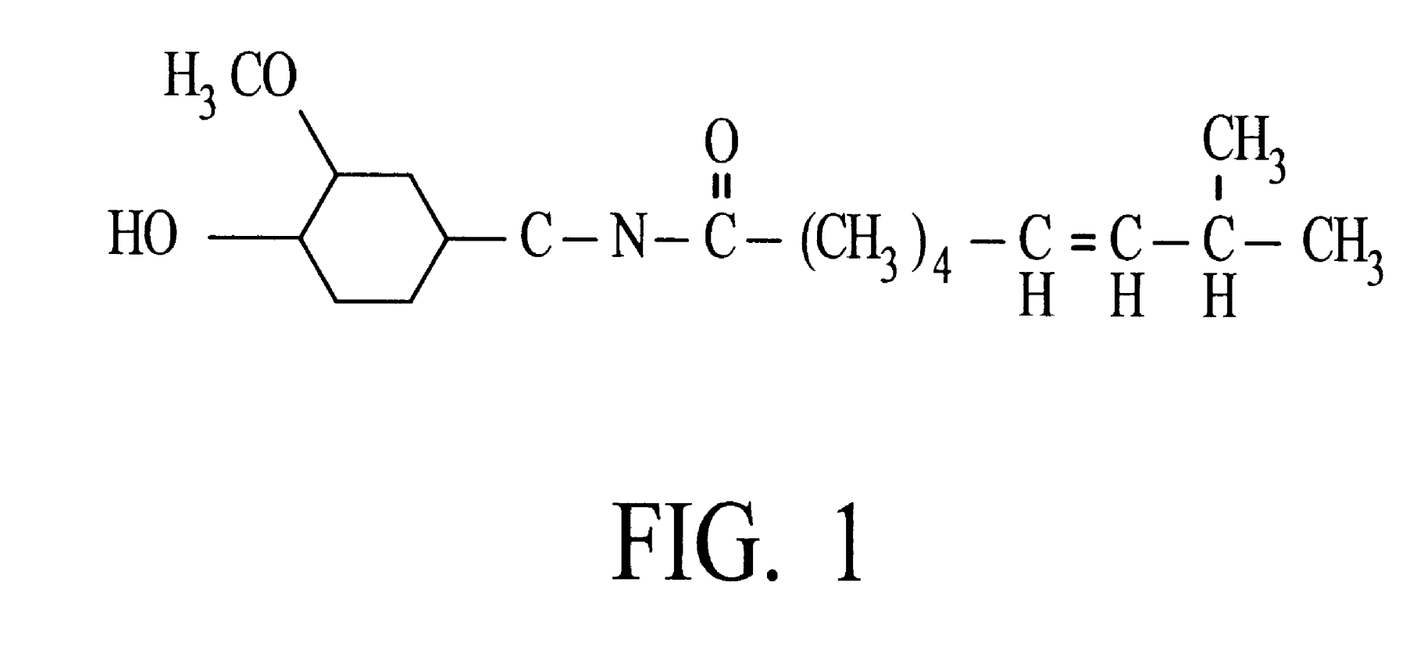
FIG. 1 is the chemical structure of capsaicin.

FIG. 1 is the chemical structure of capsicum or capsaicin 100. Capsaicin, also known as N-vanillyl-8-methyl-6-(E)-noneamide, is the most pungent of the group of compounds called capsaicinoids isolated from peppers. It is sparingly soluble in water, but very soluble in fats, oils and alcohol. The second most common capsaicinoid is Dihydrocapsaicin. Capsaicin and Dihydrocapsaicin together make up 80–90% of the capsaicinoids found in the fruit. In C. annuum the total capsaicinoid content ranges from 0.1 to 1.0%, and the capsaicin:dihydrocapsaicin ratio is about 1:1. In C. frute-scens (Tabasco peppers) the total content ranges from 0.4–1.0% with the ratio around 2:1.

The minor capsaicinoids include Nordihydrocapsaicin [Dihydrocapsaicin with (CH2)5 instead of (CH2)6], Homocapsaicin [Capsaicin with (CH2)5 instead of (CH2)4], and Homodihydrocapsaicin [Dihydrocapsaicin with (CH2)7 instead of (CH2)6]. The pungencies of these five pure compounds in Scoville Units (SU) are as follows:

| Compound | Pungency x 100,000 SU |
| --- | --- |
| Capsaicin | 160 |
| Dihydrocapsaicin | 160 |
| Nordihydrocapsaicin | 91 |
| Homocapsaicin | 86 |
| Homodihydrocapsaicin. | 86 |

Govindaraj an, VS and Sathyanarayana, MN; Capsicum—Production, Technology, Chemistry and Quality. Part V. Impact on Physiology, Nutrition and Metabolism; Structure, Pungency, Pain and Desensitization Sequences, *Crit. Rev. Food Sci. Nutr.* 29, 435. 1991 There are also homologs and analogs, such as with straight alkyl chains, that exist in nature.

Quantitation of capsicum amount in solutions is an important tool in manufacture. Following is a high performance liquid chromatography (HPLC) method for capsaicin determination: 25 g ground red pepper extracted in 200 mL 95% ethanol at 65–75 C for 5 hours, allow to settle, decant, and cool to 20 C. 50 microliters injected from a 100 microliter Hamilton LC syringe via a Waters U6K injector into a Waters HPLC system with a 10 micron micro-Bondapak C18 column and a Bondapak C18/Corasil guard column and a UV detector set at 280 nm. HPLC operated isocratically with a Waters 660 solvent programmer using a mobile phase of 40:60 v/v acetonitrile:water (1% acetic acid) at 1.5 mL per minute. Quantitation done using commercially available N-vanillyl-n-nonamide as an external standard. Hoffman, Patrick G.; Lego, Mary C.; and Galetto, William G. "Separation and Quantitation of Red Pepper Major Heat Principles by Reverse-Phase High-Pressure Liquid Chromatography" J. Agric. Food Chem. 1983, vol. 31 pp 1326–1330.

Optimally, an aqueous solution will contain between about 0.00001% and about 1.0% by weight capsaicin or capsicum. The solution can be formed using ground peppers mixed directly into water. The peppers may be dried or fresh, chopped or ground or powdered. To increase solubility of certain preparations of chilli peppers, the temperature of the water can be raised to room temperature or above. Electric or manual mixers can be employed, and it will be understood that a certain, predetermined time constant related to the solubility of the pepper material in the aqueous solution will be a factor to consider in preparing the solution.

It will be understood, therefore, that alternative methods of disinfecting and sterilizing foods, meats and equipment include injecting the killing solution, in either a powder, vapor, spray, mist or liquid form, onto the food or surface or equipment, or between some barrier component and the infestation. Said barrier component could be a plastic sheet or rubber tarp, net mesh, etc., and will be known to those skilled in the art. Additionally, the disinfecting and sterilizing solution can be applied to foods, meats, vegetables, etc., in conjunction with other food or meat additives, preparations, disinfectants, sterilizing agents, etc.

It has been observed experimentally that the rate of disinfecting and sterilizing of foods, meats and associated equipment and surfaces is often proportional to the concentration of the capsicum containing ingredients in the killing solution. It will be understood, additionally, that the term capsicum as used herein shall serve to include any material containing, but not limited to, capsicum itself, any chemically synthesized or natural extract of any plant of the genus Capsicum, any material containing capsaicin, any of the capsinoids or capsaicinoids, homologs, analogs, derivatives or similar compounds or formulations.

Solvent/Carrier

As described above, the principle solvent for the formulations of the present invention is water. Additional chemicals in the present formulation include surfactants, sticking agents, preservatives or biocidal agents, coloring dyes or agents, fragrance, etc.

In a preferred embodiment, the formulation of the present invention contains mineral oil or other food grade oil. In a preferred embodiment, the disinfecting and sterilizing solution contains a sticking agent. In a preferred embodiment, the method for disinfecting and sterilizing with an aqueous formulation containing capsicum and food grade oil whereby the aqueous formulation is a disinfecting and sterilizing solution. In a preferred embodiment, the concentration of food grade oil in the aqueous solution is about 1%, or more or less. In a preferred embodiment, the concentration of food grade oil in the aqueous solution is about 0.1% to about 100%, or more or less. In a preferred embodiment, the concentration of food grade oil in the aqueous solution is about 10%, or more or less. In a preferred embodiment, the concentration of food grade oil in the aqueous solution is about 90%, or more or less.

As described above, the addition of an inert carrier, food grade oil assists in handling of the liquid insecticidal formulations containing capsicum. Mineral or other food grade oil has been found to be a preferred additive to the present invention. Use of mineral oil in the formulation enhances dispersion, reduces fogging or misting of a potentially irritating or noxious odor. Mineral oil is non-toxic to humans, and is safe to use in households and other animal and people environments. The inert carrier oil added to the killing solution can be a combination of one or more inert carrier oils selected from the group consisting of mineral oil, organic oils, animal and vegetable oils, castor oil, hydrocarbon oils, and paraffinic oils.

Figure 2:
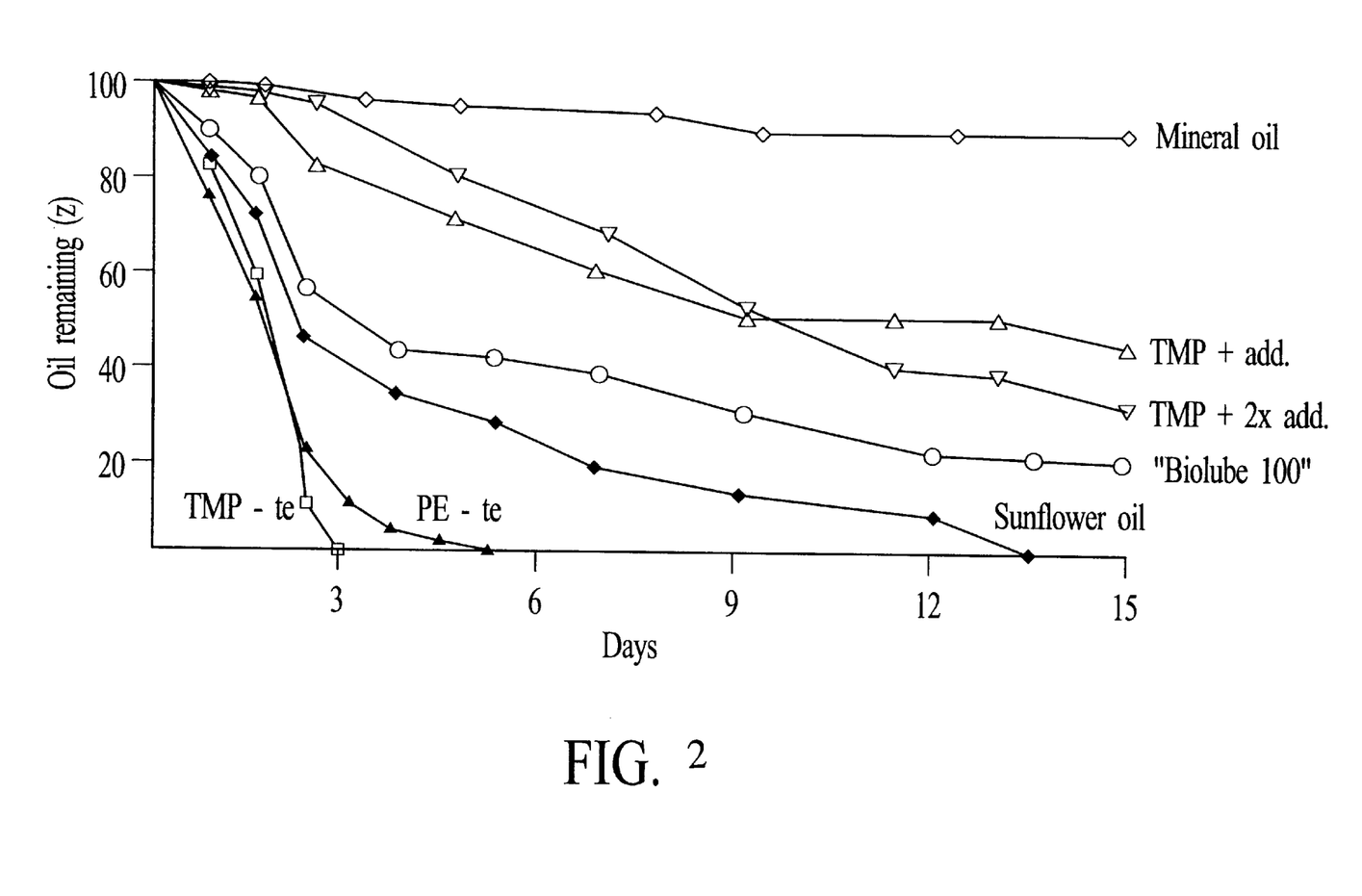
FIG. 2 is a plot showing biodegradation of different types of oils in shake flask tests.

FIG. 2 is a plot showing biodegradation of different types of oils in shake flask tests. The inoculum used is regular lake water. The oils were added at 0.01% (V/V) to M9 mineral salts medium (50 mL) in 250-mL-volume conical flasks and inoculated with 1 mL of lake water bacteria collected on a bacterial filter and resuspended to 105 cfu/mL. Flasks were incubated at 25° C. and shaken at 100 rev/min. Control flasks were poisoned with $HgCl_2$ at zero time and showed that oil disappearance by abiotic agencies was less than 7% in all cases. The oils used were: (1) mineral oil; (2) a TMP-triester; (3) a pentaerythritol tetraester; (4) sunflower seed oil; (5) "Biolube 100", a commercial fully-formulated 2-stroke oil containing a TMP-ester base oil; (6) TMP-triester with a commercial additive package added at a normal level; and (7) the same oil containing twice the normal additive level.

It will be understood that the low rates of biodegradation of mineral oils contribute to the benefit of the present invention. Mineral oils, compared to other oils, have the added benefit of being resistant to biodegradation. The residue containing the active ingredient capsicum, or other form of capsaicin, is effective as an insecticide for longer than would be possible using other forms of carrier oils.

The following table is a short list of specification for a few different types of mineral oils available:

Inert Carrier Oil Specifications

| | Spray Spec's Oil-Base | | | |
|---|---|---|---|---|
| Viscosity @ 100° F., Sus | 60-65N | 70N | 70-100N | 150N |
| Mass Boiling, % <340° C.,[1] | 35 max | 10 max | 10 max | 10 max |
| Mass Boiling, % >393°,[2] | 10 max | 35 max | 70 max | 70 max |
| Paraffinic, %,[3] | 60 min | 60 min | 60 min | 60 min |
| Aromatic, % | 3 max | 3 max | 4 max | 5 max |
| Acidity, mg KOH after exposure to UV,[4] | 0.3 max | 0.3 max | 0.1 max | 1.0 max |

[1]This temp equivalent to $C_{20}$ n-paraffin and is the lower limit for pesticidal activity.
[2]Equivalent to a $C_{24}$ n-paraffin. The fraction boiling > $C_{24}$ can be phytotoxic due to prolonged excuticular perseverance with subsequent photodegradation to toxic acids.
[3]ASTM E 1519-93 definition of paraffinic oil
[4]Modifies ASTM E 896-92, 10 mL oil in open petri dish, exposure is 365 nm UV at 2 $mW/cm^2$ for 4 hr.

It will be understood that these and other types of mineral oils and petrolatums may be used in conjunction with the killing solution of the present invention to enhance handling characteristics, residue on surfaces, etc.

Food and Meat Processing Applications

In preferred embodiments of the method and formulations of the present invention, use of a capsicum or other capsaicin-containing solution is effective in sterilizing, as an antimicrobial or sterilizing agent, for use in meat processing plants. These formulations can be used fr sterilizing other equipment and food products used in such industries. Reducing the spread of E. coli, Salmonella, and other pathogenic bacteria can be very effective when these formulations are used in restaurants, food processing and animal processing areas or facilities.

The disinfecting and sterilizing solution, comprising an aqueous formulation of capsicum or other capsaicinoid, of the present invention is effective against a range of pests and insects, including all types of: bacteria, such as E. coli, Streptococcus, Salmonella, Trichinosis, any other food-borne bacteria or pathogen, viruses, fungus, molds, and other invading pests.

Thus, the present invention is directed to the use of capsicum or other form of capsaicin for use as an disinfecting and sterilizing powder, liquid or other solution or product in food and meat preparation applications. Such include, but are not limited to, slaughtered carcasses, raw and cooked meats, corn, peas, cabbage, lettuce, watermelon, tomatoes, carrots, rhubarb, peppers of all kinds, eggplants, cannola seed, rapeseed, cannabis, apples, cherries, lemons, figs, avocados, grapefruit, oranges, limes, spice plants including herbs, parsley, cilantro, garlic, ginger, onion, potatoes, other seed crops, ornamental and edible flowers, organic vegetables, mustard, collard, chard, spinach and other greens. The addition of other additives, including mineral oil, surfactants, etc., provides a formulation which is very easy to handle, very effective anti-insecticidal, and is also environmentally non-toxic or damaging. Delivery can be any known or novel method of delivery of fluid disinfecting and sterilizing compositions to meats and foods, including but not limited to manually, via mechanical or other fluid sprinkler means, spray equipment, dusting, air drop or airplane fly-over and delivery from above, etc. The use of capsicum for this purpose, in this formulation and method of use, is heretofore unknown, is novel and unique and non-obvious, and provides unexpectedly-high satisfactory results.

It will be understood that the disinfecting and sterilizing formulation can be applied directly onto cut meat or food surfaces, or it can be applied to surfaces of equipment, handling devices, racks, containers, bins, hooks, refrigerator and freezer surfaces, transportation equipment, etc. Thus, the method of use of the present invention requires that equipment, meats, surfaces, etc. be contacted, optionally and preferably for a certain period of time, with the sterilization and disinfecting solution.

EXAMPLES

Study 1

The Use of Pepper Extract as a Possible Mortality Agent against Termites

Objective

To determine whether the active ingredients in "Habanero" peppers (assumed to be capsicum) have the ability to kill termites.

Methods

"Habanero" Pepper Solution

Ten medium sized "Habanero" peppers were finally chopped and allowed to soak for three hours in 600 mL. of purified water. The solution was then filtered into a spray bottle for experiments.

Termites:

2 termite species, commonly known as drywood and subterranean termites, were collected in the field. Twenty-five drywood termites were divided into two groups: one which contained 14 termites and one which contained 11 termites. Each group of termites was placed in a 9 cm diameter petri dish containing moistened filter paper. The first group containing 14 termites was subjected to three bursts from the spray bottle containing the pepper extract. The second group consisting of 11 drywood termites was subjected to three bursts from a spray bottle containing water only which served as a control. The same experimental design was used for subterranean termites except the treatment and control groups contained 14 and 13 termites, respectively.

Termites were maintained in their respective petri dishes for 24 hours, after which counts were made to determine the number of termites surviving for each group.

Significant differences in survivorship were compared for each species using a x2 test of independence.

Results

Data for subterranean termites are shown below. Thirteen of 14 termites were dead after 24 hrs. when exposed to pepper extract. No termites in the water controlled died in this period. This result is statistically significant based on the following computations:

| Observed | Alive (after 24 hrs.) | Dead (after 24 hrs.) | Totals frequencies |
|---|---|---|---|
| Pepper extract | 1 | 13 | 14 |
| Water control | 13 | 0 | 13 |
| Totals | 14 | 13 | 27 |

From the data we can predict expected frequencies

| Observed | Alive (after 24 hrs.) | Dead (after 24 hrs.) | Totals frequencies |
|---|---|---|---|
| Pepper extract | 7.3 | 6.7 | 14 |
| Water Control | 6.7 | 6.3 | 13 |
| Totals | 14 | 13 | 27 |

The $x^2$ value is calculated below:

$$x^2 = \frac{(|1-7.3|-0.50)^2}{7.3} + \frac{(|13-6.7|-.50)^2}{6.7} +$$
$$\frac{(|13-6.7|-.50)^2}{6.7} + \frac{(|0-6.3|-.50)^2}{6.3}$$
$$X^2 = 19.9, df = 1$$

$x^2$ Table value = 7.9 at $p = 0.005$

Because the obtained value (19.9) is greater than the table value (7.9), we can conclude that pepper extract is significantly associated with subterranean termite morality. There is only a 0.05% probability that our results were due to chance alone.

Conclusions:

Based on this experiment is concluded that "Habanero" pepper extract has the ability to kill subterranean termites under the following controlled laboratory conditions: direct contact with the pepper extract and continuous exposure to this extract for 24 hrs. in a contained environment.

Study 2

The Use of Synthetic Oleoresin as a Possible Mortality and Repellent Agent Against Ants Objective To determine whether water soluble oleoresin capsicum has the ability to kill and repel Argentine ants.

Methods

Oleoresin Capsicum Solution

Capsicum solutions were used for this experiment prepared by adding 5 and 20 mL of capsicum (250,000 scoval units) tO 45 and 30 miL of water to make solutions of 10% and 40% capsicum, respectively.

Mortality Tests

The Argentine ant (*Irdomyrnex humilis*) were collected in the field. At least 30 individual ants were placed in a 9 cm. diameter petri dish containing filter paper. Fluon was painted on the sides of dishes to prevent escape. Ants were then subjected to three bursts from a spray bottle containing the 10% capsicum extract. A similar petri dish with ants was prepared and sprayed with distilled water as a control. This experiment was then repeated using the 40% solution. Ants were maintained in their respective petri dishes for 1 hour, after which counts were made to determine the number of ants surviving for each group. Significant differences in survivorship were compared for each species using Fisher's extract test of independence.

Results

| Subjects | Alive | Dead | |
|---|---|---|---|
| Fisher Exact Test Ants 10% | | | |
| Row 1 | 30.000 | 3.000 | Counts |
| | 12.375 | 20.625 | Expected Counts |
| | 90.909 | 9.091 | Row % |
| | 100.000 | 6.000 | Column % |
| | 37.500 | 3.750 | Total % |
| Row 2 | 0.000 | 47.000 | Counts |
| | 17.625 | 29.375 | Expected Counts |
| | 0.000 | 100.000 | Row % |
| | 0.000 | 94.000 | Column % |
| | 0.000 | 58.750 | Total % |
| Fisher Exact Test Ants 40% | | | |
| Row 1 | 30.000 | 0.000 | Counts |
| | 11.538 | 18.462 | Expected Counts |
| | 100.000 | 0.000 | Row % |
| | 100.000 | 0.000 | Column % |
| | 38.462 | 0.000 | Total % |
| Row 2 | 0.000 | 48.000 | Counts |
| | 18.462 | 29.538 | Expected Counts |
| | 0.000 | 100.000 | Row % |
| | 0.000 | 100.000 | Column % |
| | 0.000 | 61.538 | Total % |

The proportion of observations in the different categories which define the contingency table is significantly different than is expected from random occurrence (P=0.001)

Conclusions

Few ants died when subjected to water alone in both experiments. However, all ants subjected to both capsicum solutions died within minutes of exposure. There was a significant difference between treatments and controls indicating that capsicum at these concentrations is lethal to Argentine ants.

Study 3
The Use of Oleoresin Capsicum as a Possible Mortality Agent against Dampwood Termites Objective To determine whether water soluble oleoresin capsicum kills dampwood termites Methods Oleoresin Capsicum Solution Dried fruit of *Capsicum frutescens* and/or *C. Annuum* measured at 500,000 Scoville heat units Mortality Tests Dampwood termites (Zootermopsis spp.) were collected in a field. Twenty individual termites were placed in a 9 cm. diameter petri dish containing filter paper. Termites were then subjected to three bursts from a spray bottle containing the capsicum extract. A similar petri dish with termites was prepared and sprayed with distilled water as a control. Termites were maintained in their respective petri dishes for each group. Significant differences in survivorship were compared using a chi-square test.

Result

Data for dampwood termites are shown below.

| Observed | Alive (after 24 hrs.) | Dead (after 24 hrs) | Totals frequencies |
|---|---|---|---|
| Pepper extract | 0 | 20 | 20 |
| Water control | 20 | 0 | 20 |
| Totals | 20 | 20 | 40 |

From this data we can predict expected frequencies

| Expected | Alive (after 24 hrs.) | Dead (after 24 hrs) | Totals frequencies |
|---|---|---|---|
| Pepper extract | 10 | 10 | 20 |
| Water control | 10 | 10 | 20 |
| Totals | 20 | 20 | 40 |

The $x^2$ value is calculated below:

$$x^2 = \frac{(|0-10|-.50)^2}{10} + \frac{(|20-10|-.50)^2}{10} + \frac{(|20-10|-.50)^2}{10} + \frac{(|0-10|-.50)^2}{10}$$
$$= 36.1$$

Formula, table values, and computations can be found in Biometry, by Sokal and Rolf.

$X^2 = 36.1$, df=1

$x^2$ Table value=7.9 at p=0.005

Because the obtained value (36.1) is greater than the table value (7.9), we can conclude that water soluble oleoresin capsicum is significantly associated with dampwood termites mortality.

Conclusions

Dampwood termites exposed to water soluble oleoresin capsicum at a concentration of 500,000 scoval units were killed on contact.

Study 4
The Use of Oleoresin Capsicum as a Possible Mortality Agent against Odorous House Ants Objective To determine whether water soluble oleoresin capsicum kills odorous house ant Methods Oleoresin Capsicum Solution Dried fruit of *Capsicum frutescens* and/or *C. Annuum* measured at 500,000 Scoville heat units Mortality Tests Odorous house ants (Tapinoma spp.) were collected in the field. Twenty individual ants were placed in a 9 cm. diameter petri dish containing filter paper. Fluon was painted on the sides of dishes tp prevent escape. Ants were then subjected to three bursts from a spray bottle containing the capsicum extract. A similar petri dish with ants was prepared and sprayed with distilled water as a control. Ants were maintained in their respective petri dishes for 1 hour, after which counts were made to determine the number of ants surviving for each group. Significant differences in survivorship were compared using a chi-square test.

Result

Data for odorous house ants are showm below.

| Observed | Alive (after 24 hrs.) | Dead (after 24 hrs.) | Totals frequencies |
|---|---|---|---|
| Oleoresin capsicum | 0 | 20 | 20 |
| Water control | 20 | 0 | 20 |
| Totals | 20 | 20 | 40 |

From this data we can predict expected frequencies

| Expected | Alive (after 24 hrs.) | Dead (after 24 hrs.) | Totals frequencies |
|---|---|---|---|
| Oleoresin capsicum | 10 | 10 | 20 |
| Water control | 10 | 10 | 20 |
| Totals | 20 | 20 | 40 |

The $x^2$ value is calculated below:

$$x^2 = \frac{(|0-10|-.50)^2}{10} + \frac{(|20-10|-.50)^2}{10} + \frac{(|20-10|-.50)^2}{10} + \frac{(|0-10|-.50)^2}{10}$$
$$= 36.1$$

Formula, table values, and computations can be found in Biometry, by Sokal and Rolf.

$X^2 = 36.1$, df=1

$x^2$ Table value=7.9 at p=0.005

Conclusions

Because the obtained value (36.1) is greater than the table value (7.9), we can conclude that water soluble oleoresin capsicum is significantly associated with odorous house ant mortality. Odorous house ants exposed to water soluble oleoresin capsicum at a concentration of 500,000 scoval units were killed on contact.

Study 5
The Use of Oleoresin Capsicum Extract as a Possible Mortality Agent against Subterranean Termites Objective To determine whether oleoresin capsicum extract mixed with mineral oil has the ability to kill subterranean termites.

Methods

Oleoresin Capsicum Solution

A capsicum solution used for this experiment was prepared by adding 0.25 grams of capsicum extract in 200 ml of light mineral oil. Mineral oil alone served as a control.

Morality Tests

Subterranean termites were collected in the field. At least 20 individual termites were placed in a 9 cm. diameter petri dish containing filter paper. Termites were then subjected to three bursts from a spray bottle containing the capsicum extract. A similar petri dish with termites was prepared and sprayed with mineral oil only as a control. Termites were maintained in their respective petri dishes for 1 hour, after which counts were made to determine the number of ants surviving for each group. Significant differences in survivorship were compared for each species using Fisher's extract test of independence.

Results

| Fisher Exact Test-Termites | | | |
|---|---|---|---|
| Subjects | Alive | Dead | |
| Row 1 | 0.000 | 20.000 | Counts |
|  | 0.000 | 20.000 | Expected Counts |
|  | 0.000 | 100.000 | Row % |
|  | (NAN) | 50.000 | Column % |
|  | 0.000 | 50.000 | Total % |
| Row 2 | 0.000 | 20.000 | Counts |
|  | 0.000 | 20.000 | Expected Counts |
|  | 0.000 | 100.000 | Row % |
|  | (NAN) | 50.000 | Column % |
|  | 0.000 | 50.000 | Total % |

Conclusions

The proportion of observations in the different categories which define the contingency table is not significantly different than is expected from the random occurrence ($P=1.000$)

All of the termites exposed to the capsicum mixed with mineral oil died within seconds. From this data we can conclude that capsicum mixed with mineral oil has an impact on termite mortality.

Further testing has shown that the killing solutions described herein are effective, long-lasting, and environmentally friendly. While lethal to insects, including spiders, ants and termites, the active ingredient capsicum or other form of capsaicin and the inert carrier oil such as mineral oil are all safe for use in the Ienvironment, are essentially non-toxic to humans in the concentrations used herein, and are readily available.

Study 6

The following is a set of further experiments listed chronologically, in the order in which they were performed:

Friday, Jul. 14, 2000

First mixed a solution of 1% Capsin and sprayed four flea beetles and two cabbage seed pod weavils and one lygus bug. After one minutes, one flea beetle was not moving. At five minutes, three were still. After fourteen minutes the flea beetles and the cabbage seed pod weavils were all dead. It took fifty-six minutes to kill the lygus bug. Sprayed some bugs on a canola plant out in the field. Marked the plant for observation and watched the flea beetles drop off and crawl away. For the testing used a glass vial to hold bugs and a fine misting spritzer bottle to spray the bugs. Used three squirts for the first two tests.

3. Collected a small sack of canola insects and dumped them into a large Coleman cooler with a screen over the top., containing approximately 100 flea beetles and 20 cabbage seed pod weavils. Sprayed the 1% solution over the top of them and observed. After ten minutes the bugs appeared quiet, after thirty minutes bugs became very active. Added a little more mist at thirty-three minutes, at forty-seven minutes bugs appear still but move or jump when probed with a pencil. Sixty-two minutes bugs appear healthy. Started new vial test. One hundred-ten minutes the flea beetles in vial barely alive. Bugs in cooler very healthy again. Next morning, bugs in vial dead. 40% of flea beetle in cooler are dead. No dead cabbage seed pod weavils.

4. 3% solution and re-sprayed "live" cooler bugs. Fifteen minutes later flea beetles were dead and one cabbage seed pod weavil that was hit directly. Fresh cabbage seed pod weavil in vial with one blast of 3% solution. Ten minutes the bug is dead. Five hours late no more bugs are dead. The rest are still unaffected. It appears it takes a complete saturation for prolonged period to kill bugs.

Jul. 20, 2000

Rechecked canola plants in field and they appear to be clear from insects although hardly any insects exist now due to the whole field being sprayed by air with Capture for a bad cabbage seed pod weavil infestation.

Aug. 10, 2000

Four rows of canola planted in a big planter. Rows were 18 inches long with 6 inch spacing. One row treated with 5% water capsicum solution, one with 5% capsicum and canola oil and one with 5% capsicum with mineral oil. With one row of untreated "control". After five days observed the test and saw that it was germinating. Moved the test outside and introduced it to insects.

Aug. 20, 2000

Observed test and saw that the seedlings were being eaten by insects. Three days later the plants were dead.

Aug. 28, 2000

Sprayed mature plants along field edges with 5% Capsicum solution and observed insects dropping off immediately, bugs appeared to die within minutes, but it was hard to tell if they would recover, like previous tests. This test was to determine if Capsicum would keep bugs off of the plants. After test conducted, it rained for about one week. When returned observed no bugs on any plants anywhere. Even where didn't spray.

Study 7

Viability of *E. Coli* Following Exposure to Capsaicin

The following study was performed to determine viability of *E. coli* bacteria following exposure to aqueous solution containing capsaicin.

Day 1

Take organism: *E. coli* from stock

Inoculation as follows

A 1. 100% pepper solution (suspended in TSB Broth)

+0.1 ($100_1$) of *E. coli*

2. 50% pepper solution (1 cc of pepper solution +1 cc of TSB Broth)

+0.1($100_2$) if *E. coli*

3. 25% pepper solution (1 cc of pepper solution +1.5 cc of TSB)

+0.1 ($100_1$) of *E. coli*

4. 10% pepper solution (0.1 cc of pepper solution +0.9 cc of TSB Broth

B. Serial dilution of pepper solution

| 100% 1 cc ▶ | 50% | ▶ | 25% | ▶ | 12.5% |
|---|---|---|---|---|---|
| | 1 cc of Broth | + | 1 cc of Broth | + | 1 cc of Broth + |
| | | | | | 0.1 ($100_2$) E. coli suspended in TSB |

Incubation of all tubes at 35°

| Day 2 | Substituted all tubes to TBA (total blood sugar) Incubation at 35° |
|---|---|
| Day 3 | Reading the plates |

| A | 100% pepper solution ng | 50% ng | 25% growth | 10% growth |
|---|---|---|---|---|
| B | 100% ng | 50% (1:2) ng | 25% (1:4) growth | 12.5% (1:8) growth |

Negative control = TSB – no growth
Positive control TBS + 0.1 *E. coli* – growth Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A sterilizing and disinfecting formulation for killing bacteria on contact, the sterilizing and disinfecting formulation containing water and between about 0.0001 percent and about 10.0 percent by weight capsicum.

2. The sterilizing and disinfecting formulation of claim 1 in which the concentration of capsicum is between about 0.001 and about 1.0 percent by weight.

3. The sterilizing and disinfecting formulation of claim 2 in which the concentration of capsicum is between about 0.01 and about 0.1 percent by weight.

4. The sterilizing and disinfecting formulation of claim 1 in which the concentration of water 2! is between about 90.0% and about 99.9999%.

5. The sterilizing and disinfecting formulation of claim 1, further comprising an inert carrier oil.

6. The sterilizing and disinfecting formulation of claim 5 in which the inert carrier oil is a combination of one or more inert carrier oils selected from the group consisting of mineral oil, organic oils, animal and vegetable oils, castor oil, hydrocarbon oils, and paraffinic oils.

7. The sterilizing and disinfecting formulation of claim 5 in which the concentration of inert carrier oil is between about 0.001 and about 99%.

8. The sterilizing and disinfecting formulation of claim 7 in which the concentration of inert carrier oil is between about 0.01 and about 10%.

9. The sterilizing and disinfecting formulation of claim 8 in which the concentration of inert carrier oil is between about 0.1 and about 1%.

10. A method for disinfecting and sterilizing surfaces consisting of contacting the surfaces with an aqueous formulation containing capsicum.

11. The method of claim 10 in which the aqueous formulation contains between about 0.001% and about 10% capsicum.

12. The method of claim 10 in which the aqueous formulation contains between about 0.01% and about 5% capsicum.

13. The method of claim 10 in which the surfaces are used for food processing.

14. The method of claim 10 in which the surfaces are used for meat processing.

15. A method for disinfecting and sterilizing surfaces containing bacteria consisting of contacting the surfaces with an aqueous formulation containing capsicum.

16. The method of claim 15 in which the bacteria comprise those selected from the group consisting of *E. coli*, Salmonella, Trichinosis.

17. The method of claim 15 in which the bacteria comprise those selected from the group consisting of food-borne pathogenic bacteria.

18. The method of claim 15 in which the surfaces are contacted with the sterilizing and disinfecting formulation by rinsing the surfaces with the formulation.

19. The method of claim 15 in which the surfaces are contacted with the sterilizing and disinfecting solution for between about 0.01 minutes and about 10 minutes.

20. The method of claim 19 in which the surfaces are contacted with the sterilizing and disinfecting formulation for between about 0.1 minutes and about 5 minutes.

* * * * *